United States Patent [19]

Lundy et al.

[11] Patent Number: 4,665,485

[45] Date of Patent: May 12, 1987

[54] METHOD AND APPARATUS FOR CHARACTERIZING THE UNKNOWN STATE OF A PHYSICAL SYSTEM

[75] Inventors: Joseph R. Lundy, New York; Thomas J. Kazlausky, Woodhaven, both of N.Y.

[73] Assignee: Lundy Research Laboratories, Inc., New York, N.Y.

[21] Appl. No.: 631,743

[22] Filed: Jul. 17, 1984

Related U.S. Application Data

[63] Continuation-in-part of Ser. No. 516,477, Jul. 22, 1983, Pat. No. 4,570,225.

[51] Int. Cl.$^4$ .......................... G06F 15/42; G06F 7/60
[52] U.S. Cl. ..................... 364/417; 364/422; 364/516; 364/551; 128/697; 128/699; 128/700; 128/702; 128/710
[58] Field of Search .............. 364/417, 422, 551, 516, 364/830, 415–416; 128/697, 699, 700, 702, 710

[56] References Cited

U.S. PATENT DOCUMENTS

| | | | |
|---|---|---|---|
| 3,442,264 | 5/1969 | Levitt | 128/2.06 |
| 3,602,706 | 8/1971 | Levitt | 235/193 |
| 4,570,225 | 2/1986 | Lundy | 364/417 |

OTHER PUBLICATIONS

"Proposal for Study of the Uses of a Novel Display Technique for Identification of Classes of Observed Data", General Electric Proposal (GE-RSD Proposal No. N 70166), submitted to Advanced Research Projects Agency of the U.S. Dept. of Defense, Aug. 1964.

Primary Examiner—Jerry Smith
Assistant Examiner—Charles B. Meyer
Attorney, Agent, or Firm—Morgan & Finnegan

[57] ABSTRACT

A method and an apparatus are disclosed for characterizing the unknown state of a physical system having a time varying history, the characterization being made with reference to a known state of like physical systems. A response signature representative of the unknown system state is compared to a standard signature representative of the known system state. The standard signature includes a primary signature comprising a multi-dimensional region within a pre-defined, transformed coordinate system having an inner and outer boundary, and a secondary signature comprising at least one, but preferably two or more isoclines situated within the bounded region. If the response signature lies wholly within the bounded region and does not cross any of the region's isoclines, the system being characterized is deemed to be in the known state. Conversely, if both of these criteria are not satisfied the relative degree of departure of the system in the unknown state from the known system state is predicted using one or more point functions representative of the system being characterized. The ability to characterize the state of a physical system can be enhanced by adjusting the coordinate transformations of the standard signature and the response signature by and offset factor, and by subsequently subjecting both signatures to a topological transformation which produces a standard signature comprised of two concentric geometric figures.

18 Claims, 22 Drawing Figures

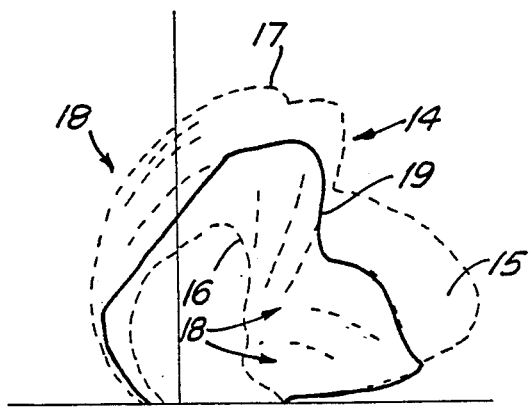
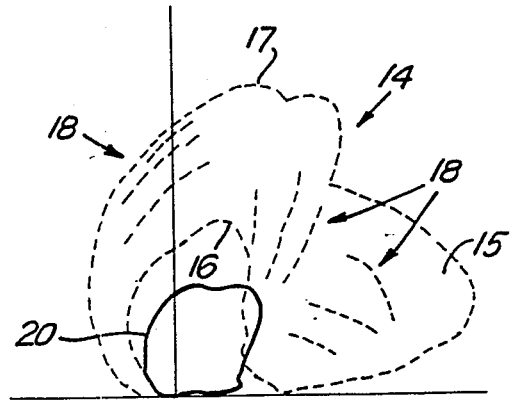
FIG.6  FIG.7
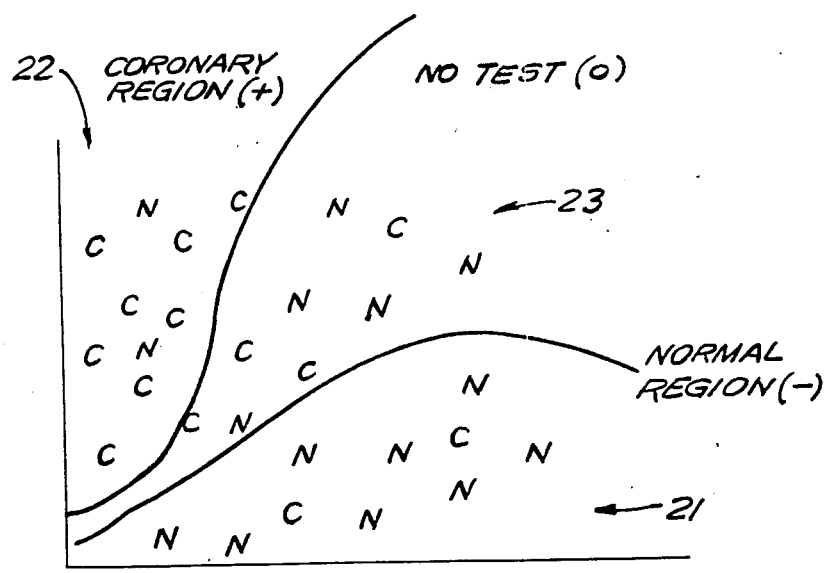
FIG.8

METHOD AND APPARATUS FOR CHARACTERIZING THE UNKNOWN STATE OF A PHYSICAL SYSTEM

This is a continuation-in-part application of pending application Ser. No. 516,477, filed July 22, 1983, now U.S. Pat. No. 4,570,225, issued 2/11/86.

BACKGROUND OF THE INVENTION

The present invention relates to the field of electronic signal processing, and more particularly to a method and an apparatus for characterizing the unknown state of a physical system having a time varying history, the characterization being made with reference to a known state of like physical systems.

For many physical systems the ability to predict accurately the future state of the system is as important as, and in some instances more important than, knowledge of the present state of the system. For example, in the field of medical science the ability to predict future medical problems of seemingly healthy individuals is of paramount importance. Although this ability is extremely desirable, such predictions based on presently known techniques are often inaccurate.

Illustrative of this problem is the current limited ability to predict from early symptoms the onset of coronary problems in the future in a seemingly normal individual who presently exhibits a negative electrocardiographic reading and who as no prior history of heart disease or problems typically associated therewith. Currently, techniques exist for analyzing electrocardiographic data. For example, an article by Teichholz et al., 35 The American Journal of Cardiology 531-36 (April 1975), entitled "The Omni Cardiogram, New Approach To Detection Of Heart Disease In Patients With A Normal Resting Cardiogram", discusses a technique for analyzing and detecting subtle degrees of abnormality not apparent in raw electrocardiographic data. Although the analytical technique described in this article possesses certain desirable attributes and results in a better understanding of the underlying data, it still has certain drawbacks and limitations. More specifically, it does not enable one to predict accurately and quantitatively the future onset of coronary disease in a patient possessing an apparently normal electrocardiogram. It is believed that prior to the present invention this problem has gone unsolved.

Accordingly, it is a general object of the present invention to overcome the drawbacks and limitations of known signal processing systems for characterizing the state of a physical system when it is unknown.

It is a specific object of the present invention to provide a method and an apparatus for evaluating the present state and/or predicting the future state of a physical system.

It is another object of the present invention to provide a method and an apparatus for characterizing the state of a medical system with reference to a known state of like systems.

SUMMARY OF THE INVENTION

The foregoing and other objects and advantages which will be apparent in the following detailed description of the preferred embodiment, or in the practice of the invention, are achieved by the invention disclosed herein, which generally may be characterized as a method and an apparatus for characterizing the unknown state of a physical system, the characterization being made with reference to a known state of like physical systems.

In accordance with the teachings of the present invention, a response signature representative of the unknown system state is obtained and compared to a standard signature representative of the known system state to determine whether the system being characterized is in the known state, and, if not, the relative degree of departure therefrom.

The ability to ascertain and evaluate quantitatively the relative degree of departure of the unknown system state from the known system state is provided by applicant's discovery that useful data is obtained if the standard signature is further refined to include at least a primary signature comprising a multi-dimensional region within a pre-defined non-linear coordinate system having an inner boundary and an outer boundary, and a secondary signature comprising at least one, but preferably two or more isoclines situated within the bounded region.

If the response signature lies wholly within the bounded region, and does not cross any of the isoclines situated therein, the system being characterized is deemed to be in the known state. Conversely, if the two criteria are not satisfied the system is deemed to be in a state other than the known state. The relative degree of departure of the unknown system state from the known system state is evaluated using one or more point functions representative of the system being characterized. More specifically, a number representative of the relative degree of departure of the unknown system state from the known system state is obtained by weighting each of the point functions by a pre-determined factor and summing the weighted point functions.

BRIEF DESCRIPTION OF THE DRAWINGS

Serving to illustrate an exemplary embodiment of the invention are the drawings of which:

FIG. 6 illustrates a transformed normal EKG within the normal EKG template.

FIG. 7 illustrates a transformed seemingly normal EKG outside the normal EKG template.

FIG. 8 illustrates a plot of the point function $P_1$.

DETAILED DESCRIPTION OF THE PREFERRED EMBODIMENT

The teachings of the present invention are applicable to the characterization of various types of physical systems having a time varying history. Although, it will be described primarily in conjunction with the analysis of electrocardiographic data obtained from animate subjects, other applications for the present invention will also be discussed.

Figure 1:
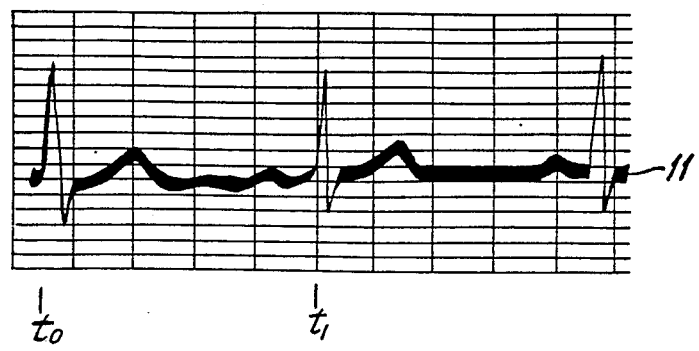
FIG. 1 illustrates a normal EKG.

FIG. 1 illustrates an electrocardiogram 11 taken from a truly normal subject. As shown therein, the electrocardiographic signal is time-varying and periodic, i.e., it starts at a time $t_0$ and ends at a time $t_1$, at which point it repeats itself. Electrocardiographic signal 11 is exemplary of actual electrocardiograms taken from a human control group consisting of caucasian males between the ages of 28 and 72. As one skilled in the art will appreciate, the electrocardiographic data representative of other major groups of medical subjects may differ somewhat from this particular control group.

Figure 2:
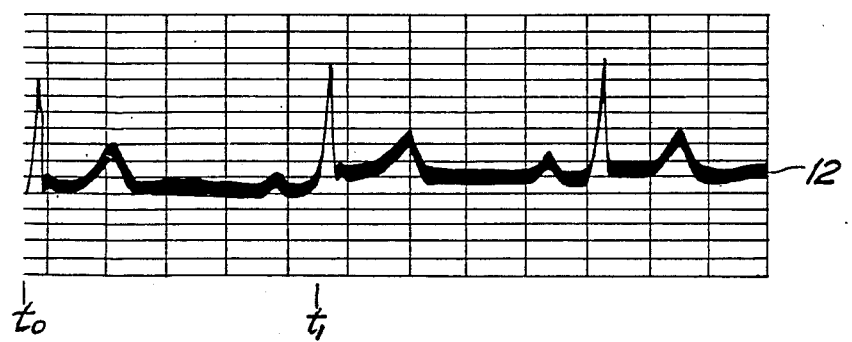
FIG. 2 illustrates a seemingly normal EKG.

FIG. 2 illustrates an electrocardiogram 12 taken from a seemingly normal, i.e., pre-coronary, subject. It is also a periodic time-varying signal, and is exemplary of electrocardiograms taken from a human control group consisting of caucasian males between the ages of 28 and 72, all of whom had a coronary episode within five years after the taking of their electrocardiogram.

Visually, electrocardiographic signal 11 does not appear to differ significantly from electrocardiographic signal 12. However, as noted above, the members of the control group from which the data presented in FIG. 1 was obtained did not experience a coronary episode within ten years, if at all, after the taking of their electrocardiogram, whereas the members of the control group from which the data presented in FIG. 2 was obtained did experience a coronary episode within five years after the taking of their electrocardiogram. Hence, this latter data is characterized as being taken from a seemingly normal subject.

According to the present invention the differences between data obtained from a truly normal subject, exemplified by FIG. 1, and data obtained from a seemingly normal, or latent coronary subject, exemplified by FIG. 2, can be enhanced by plotting the data in polar coordinates obtained using the following non-linear transformation:

$$\phi = \frac{\int_{t_0}^{t} |v|\, dt}{\int_{t_0}^{t_1} |v|\, dt} \tag{1}$$

$$r = |\phi - f(T)| \tag{2}$$

$$\theta = \pi T \tag{3}$$

where
V(t) is the time-varying signal of the electrocardiogram;
|V(t)| is the absolute value of V(t);
t is the variable time;
$t_0$ is the point in time at which the electrocardiographic data acquisition process is initiated;
$t_1$ is the point in time at which the waveform V(t) repeats itself;
$\phi$ is the integrated, normalized representation of the time varying signal V(t);
r is the radius vector of the transformed electrocardiographic data;
$\theta$ is the angle of the radius vector r;
T equals $t/t_1$; and
f(T) is an arbitrarily selected predetermined function of the normalized variable T which may be chosen as a straight line (see FIG. 3) or the average of a group of normal curves, or the average of a group of non-normal curves.

Figure 4:
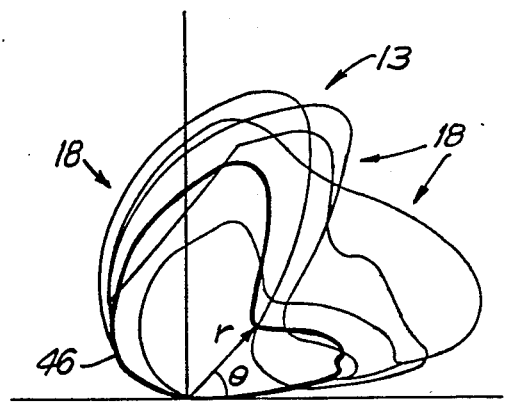
FIG. 4 illustrates transformed normal EKGs in polar coordinates.
Figure 5:
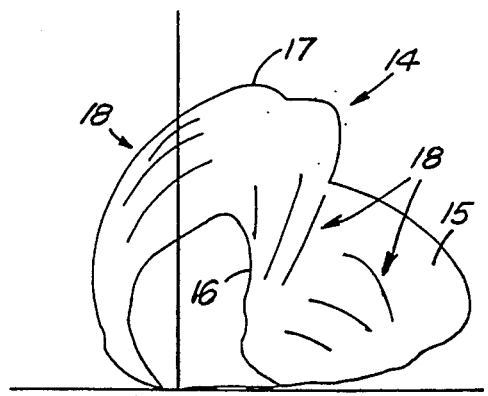
FIG. 5 illustrates a normal EKG template with isoclines.

When Equations (2) and (3) are plotted in polar coordinates for data representing electrocardiograms obtained from truly normal subjects, curves such as the curves 13 illustrated in FIG. 4 are obtained. Once the data representative of a sufficient number of normal cases has been plotted, a corresponding standard signature composite template can be formed. The template 14 for curves 13 is shown in FIG. 5. It includes a primary signature portion comprising a closed two dimensional region 15 within a pre-defined transformed coordinate system having an inner boundary 16 and outer boundary 17 derived from the curves 13 of FIG. 4; and a secondary signature portion comprising segments or isoclines 18 of some of the normal curves 13 which are substantially, or nearly, parallel. These segments or isoclines are emphasized in FIG. 5.

Isoclines 18 further subdivide the "normal" region 15 between the inner and outer boundaries thereof, and are utilized as follows. Referring to FIG. 6, the standard signature template 14 shown in FIG. 5 is shown therein in phantom to emphasize that a truly normal electrocardiographic signal plot 19 lies wholly within the inner and outer boundaries 16 and 17 of the closed region 15 comprising the primary portion thereof and does not cross any of the secondary isoclines 18 situated therein. In contrast, a seemingly normal electrocardiographic signal plot 20 obtained from a pre-coronary subject will, as shown in FIG. 7, either fall, partially or entirely, without bounded region 15 of template 14 (also shown in phantom for emphasis purposes), or if entirely within the bounded region will cross one or more of the isoclines 18 situated therein. It is these characteristic conditions which identify pre-coronary subjects who would otherwise appear normal using known diagnostic techniques.

In accordance with the present invention, a response signature (polar plot) is made for each of the standard electrocardiographic leads utilized to obtain data from a test subject, and compared to a corresponding standard signature template. Although there are twelve standard electrocardiographic leads, the principles of the present invention will be illustrated in conjunction with a discussion of the I, II, $V_4$ and $V_6$ leads. However, it is noted that the teachings of the present invention may be applied to as few as one or as many as twelve electrocardiographic leads.

Comparisons between the response signatures of the utilized cardiographic leads and the corresponding standard signature templates is readily effected by overlaying the transformed response signature and its corresponding standard signature template. If a transformed response signature for any of the above-noted electrocardiographic leads falls without the boundaries of the corresponding standard signature template or crosses one or more isoclines situated within the bounded region therein, it is deemed positive and assigned a value of $+1$. Similarly, if a transformed response signature for any of the above-noted electrocardiographic leads falls entirely within the boundaries of the corresponding standard signature template and does not cross any of the isoclines situated within the bounded region, it is deemed negative and assigned a value of $-1$. For any transformed response signatures for which none of the above conditions are apparent it is deemed inconclusive and assigned a value of zero.

The present invention also utilizes point functions which, in contrast to what might be characterized as path functions which display an entire signal waveform as a transformed line, compress essential geometric features of an original signal waveform or a transformed signal waveform into single points. Illustrative examples, as applied to the subject of the present discussion, are the area of the electrocardiographic signal, the arc length of the electrocardiographic signal, the area of the $\phi,T$ signal, the arc length of the $\phi,T$ signal, the area of the $r, \theta$ curve, and the arc length of the $r, \theta$ curve.

It has been found that better predictive results are achieved when the above-identified point functions are combined in a non-dimensionalized form and plotted with respect to one another. Illustrative examples of such point functions by coordinates are the following:

$P_1 = [$(electrocardiographic signal arc length)$^2 \div$(electrocardiographic signal area), versus $(\phi,T$ arc length$)^2 \div (\phi,T$ area$)]$ $P_2 = [$(electrocardiographic signal arc length)$^2 \div$(electrocardiographic signal area), versus $(r, \theta$ arc length$)^2 \div (r, \theta$ area$)]$ $P_3 = [(\phi,T$ arc length$)^2 \div (\phi,T$ area), versus $(r, \theta$ arc length$)^2 \div (r, \theta$ area$)]$ It is noted that point functions, $P_1$, $P_2$ and $P_3$ are examplary and do not represent the total number of possible point functions for a given signal waveform. Nevertheless, for electrocardiographic data evaluation it has been found that optimum results, i.e., a maximum detection rate and a minimum false positive rate, are obtained by utilizing seven sets of data obtained from the test subject, i.e., data obtained from the I, II, $V_4$ and $V_6$ electrocardiographic leads and the point functions, $P_1$, $P_2$ and $P_3$, defined above.

The data exhibited in FIG. 8 were obtained by calculating and plotting $P_1$ for a large group of test subjects. As shown therein, the data fell into three definable regions. One region 21 contains a clustering of data points, (denoted by N's) obtained from normal test subjects; another region 22 contains a clustering of data points (denoted by C's), obtained from pre-coronary test subjects, and the third region 23 contains a mixed clustering of N's and C's and thereby precludes meaningful data discrimination. The three regions of FIG. 8 are separated by curved lines which may be fitted to the plotted data by means of curve fitting techniques for maximum accuracy.

The same procedure previously described for the electrocardiographic lead data is followed for each of the point functions. Using data obtained from a test subject, or transformed data representative thereof, the $P_1$, $P_2$ and $P_3$ point functions are calculated and plotted on the standard $P_1$, $P_2$ and $P_3$ plots, respectively. If the calculated point function yields a value which falls within the pre-defined clustering of N points 21 it is deemed negative and assigned a value of $-1$; if the calculated point function yields a value which falls within the pre-defined clustering of C points 22 it is deemed positive and assigned a value of $+1$; and if the calculated point function yields a value which falls within the pre-defined clustering of N and C points 23 it is deemed inconclusive and assigned a value of zero.

Multiplicative weighting factors, which may vary for each of the electrocardiographic leads and point functions, are assigned to the numerical constants $\pm 1$ or zero. In general, these weighting factors are developed using empirical data obtained from actual population samples. Specifically, electrocardiogram data are obtained from each of the individuals in the population sample. The subsequent coronary history of each of the sample members is then monitored to identify a sub-sample group of "normal" individuals. A normal standard signature template is then developed from the sub-sample group.

The specific weighting factors are obtained by trial and error using a computer to carry out multiple iterations of number substitutions until corresponding results are achieved. The final selection of the weighting factors is based on the desired detection rate and/or the false positive rate. The detection rate is defined as the percentage of sick subjects detected as sick, while the false positive rate is defined as the percentage of normal subjects detected as sick. Depending upon the particular application, the weighting factors will be selected to adjust one variable or the other.

For example, where the present invention is used to screen potential pilots for the Air Force, it is desirable to select the weighting factors to maximize the detection rate. In this instance there would be little effort to minimize the false positive rate.

For an insurance company seeking to screen potential insureds the weighting factors would be selected to minimize the false positive rate. In this instance a relatively low detection rate would be satisfactory. As one skilled in the art will appreciate, the two variables are interdependent, but not complimentary.

Thus, for the four lead, three point functions electroardiographic system described above, the weighting factors selected would depend upon the particular application in which the present invention is used and the section of the population to which the test subject belonged.

The weighted sum of the test data, i.e., electrocardiographic test lead data and calculated point function values, is designated as the Lundy index and is given by the following expression:

$$L = \sum_{i=1}^{n} W_i N_i \qquad (4)$$

where n = the number of different tests utilized $W_i = i^{th}$ weighting factor $N_i = i^{th}$ numerical constant $(0, \pm 1)$.

As will be illustrated in more detail below, the value, i.e., magnitude and sign, of the Lundy index provides a valuable tool in analyzing and predicting the likelihood that a particular test subject is going to experience a future coronary episode.

The data tabulated in table I below illustrates the teachings of the present invention to test data obtained from six different test subjects. As illustrated therein, seven types of data were obtained for each of the test subjects. In particular, evaluation data were obtained from the I, II, $V_4$ and $V_6$ electrocardiogram test leads; and, in addition the $P_1$, $P_2$ and $P_3$ point functions were calculated in conjunction with the electrocardiographic data obtained from the leads.

Examining the data from Table I obtained for the second subject illustrates the teachings of the present invention. Specifically, since the transformed response signal corresponding to the data obtained with the electrocardiographic lead I was found to lie wholly within the bounded region of the composite standard signature template for lead I and did not cross any of the isoclines situated therein, it was deemed to be negative and was assigned a value of −1. Since the transformed response signal corresponding to the data obtained with the electrocardiographic lead II was found to be wholly within the bounded region of the composite standard template for lead II but crossed one or more of the isoclines situated therein, it was deemed to be positive and was assigned a value of +1. Similarly, since the transformed response signal corresponding to the data obtained with the electrocardiographic lead $V_4$ was found to be not wholly within the bounded region of the composite template for lead $V_4$, it was deemed to be positive, and assigned a value of +1. And finally, since the transformed response signal corresponding to the data obtained with the electrocardiographic lead $V_6$ was not found to satisfy clearly any of the above conditions, it was deemed to be inconclusive and assigned a value of zero.

The three point functions, $P_1$, $P_2$ and $P_3$, were calculated and plotted on the respective response templates for the $P_1$, $P_2$ and $P_3$ functions. Since each one was found to fall in the C (pre-coronary) region (e.g., region 22 of FIG. 8), it was deemed to be positive and assigned a value of +1.

The next step was to calculate the value of the Lundy index for the test subject. To determine this value the respective numeral constants were multiplied by the corresponding weighting factors. As noted in Table I, the factors for the I, II, $V_4$ and $V_6$ electrocardiograph leads were empirically determined in accordance with the criteria articulated above to be 2, 5, 3 and 1, respectively. Similarly, the factors for the $P_1$, $P_2$ and $P_3$ point functions were determined to be 2, 1 and 3, respectively.

Accordingly, the Lundy index, L, for this subject is equal to the weighted sum of (2) (−1)+5(+1)+(3) (+1)+(1) (0)+2(+1) 3(1) or +12. Since this number is positive, this case is designated as a coronary candidate.

Accordingly, the significance of the Lundy index as a diagnostic tool in indicating the probability that, and the approximate length of time before a coronary episode will occur in the absence of medical intervention is apparent. In particular, an inverse relationship between the Lundy index and the length of time before an episode is indicated, i.e., a large positive Lundy index indicates a short interval to the coronary episode. Conversely, a direct relationship between the Lundy index and the probability of a future coronary episode is indicated, i.e., a large positive Lundy index indicates a strong probability that a coronary episode will occur. The larger this index, the greater the probability and the shorter the time. A negative Lundy index, indicates freedom from heart disease. The more negative it is, the greater is the degree of certainty regarding the absence of heart disease.

Figure 9:
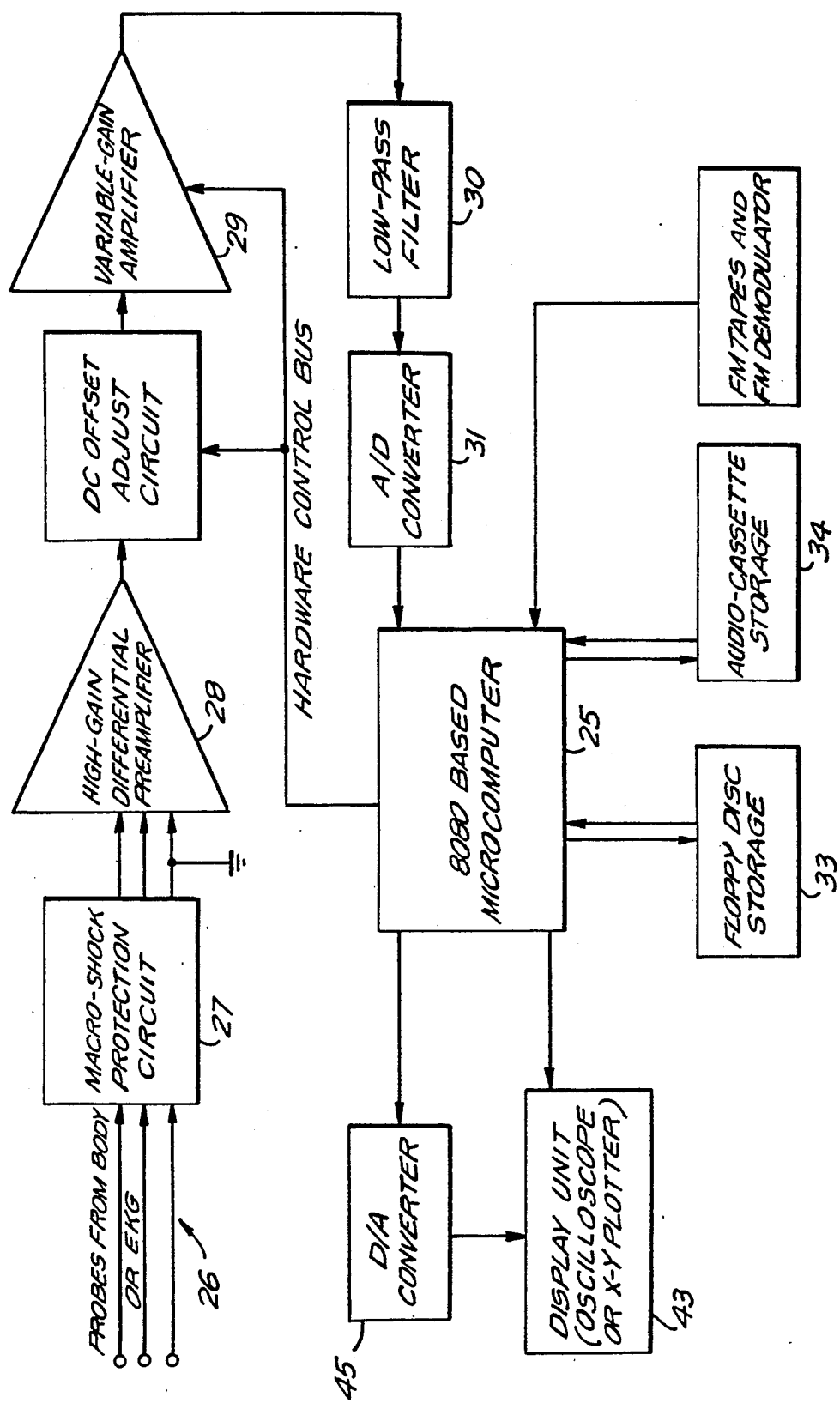
FIG. 9 illustrates a block diagram of a signal processing system for carrying out the present invention.

FIG. 9 is a block diagram of a system that can be utilized to implement the exemplary embodiment of the present invention. The heart of the system is a microprocessor based computer 25.

Figure 10A:
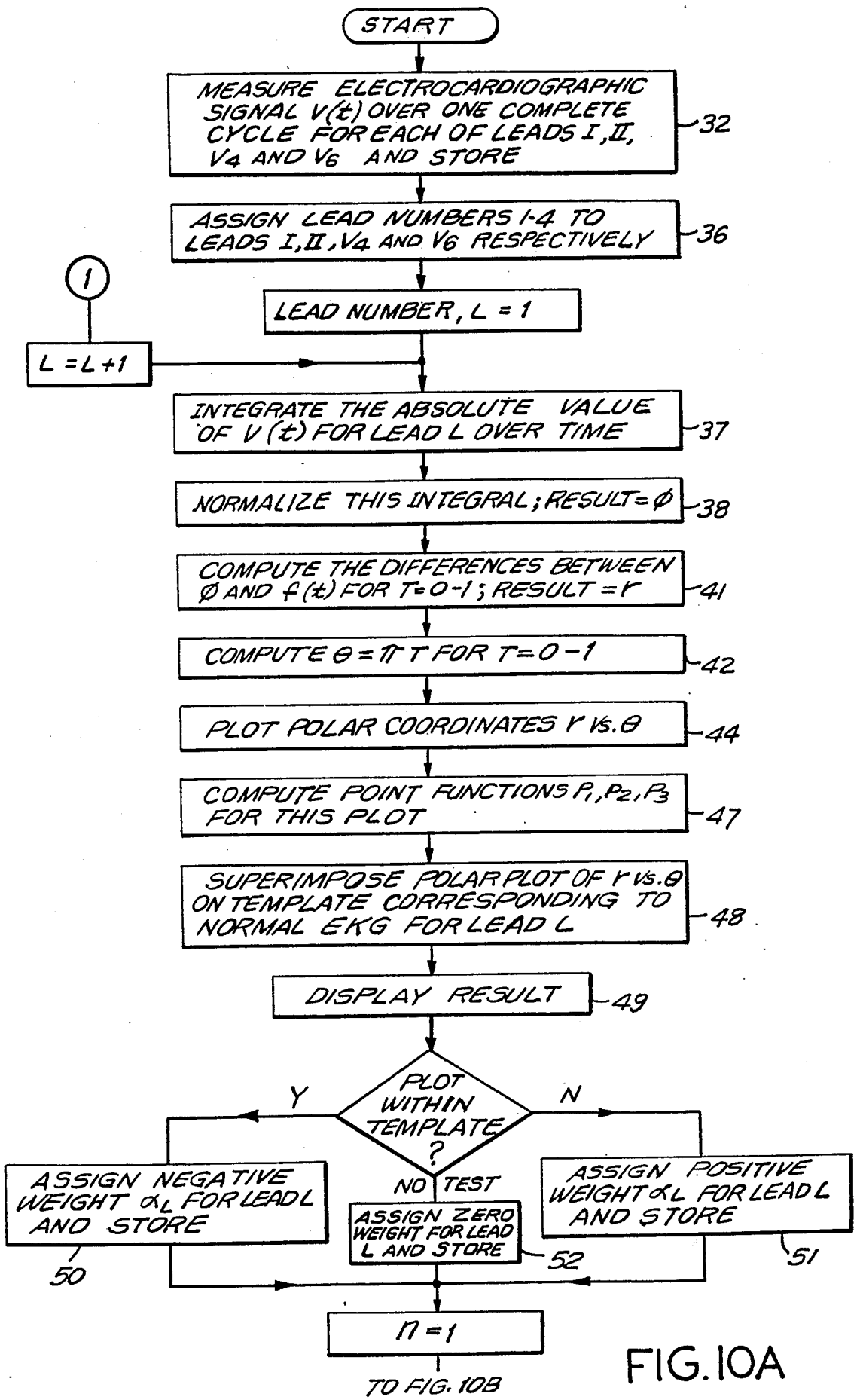
FIGS. 10A and B illustrate a flowchart of the method of the present invention.
Figure 10B:
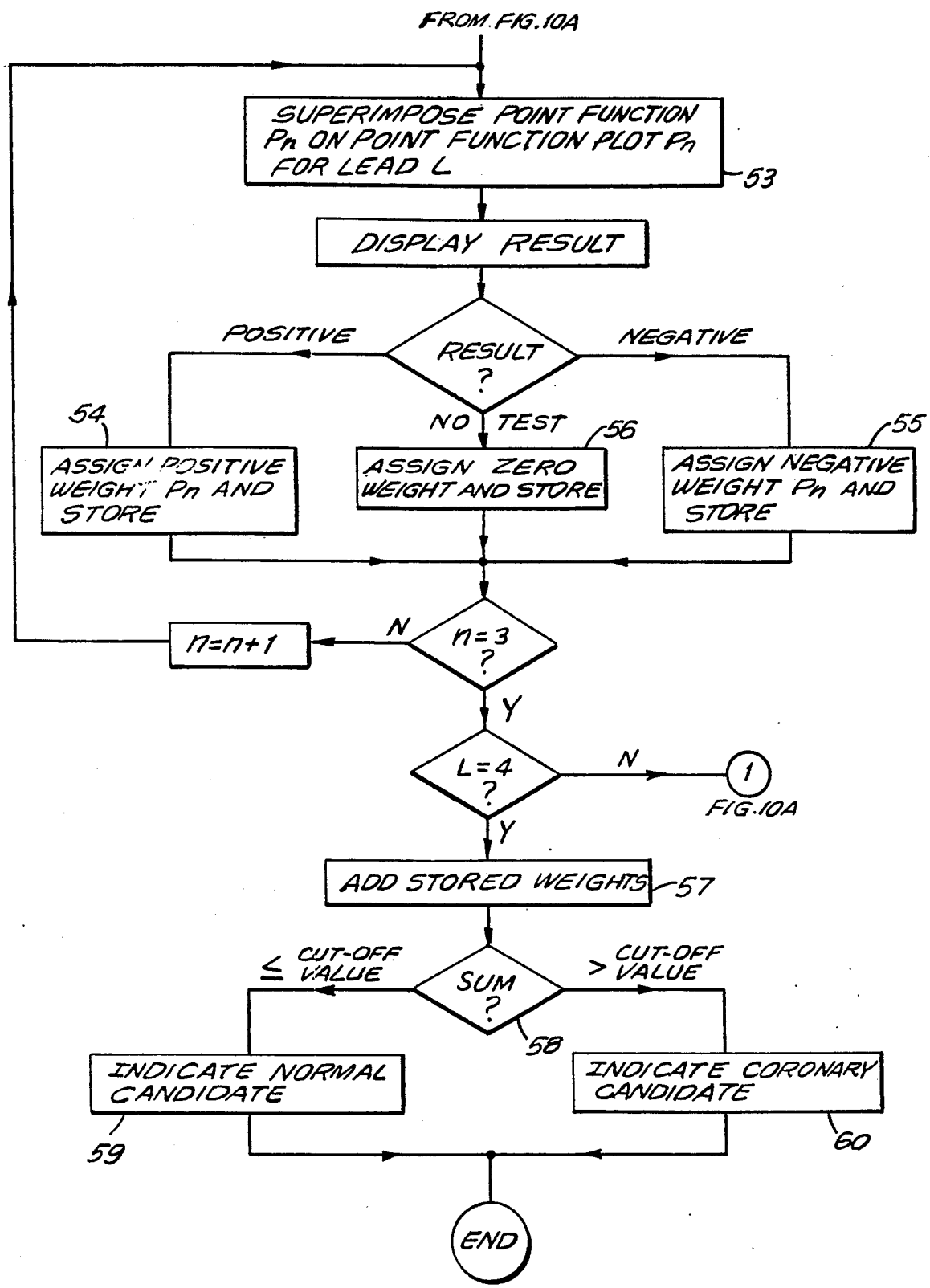

FIGS. 10A and 10B illustrate a flow chart of the method of the present invention. It can be used as the basis for a program utilized by microcomputer 25 to carry out the method of the present invention. As shown in FIGS. 10A and 10B, the method steps of the invention include the acquisition, intergration, normalization, transformation and comparison of data representative of a pre-defined physical state. These steps will be discussed in detail in conjunction with both the block diagram of the system illustrated in FIG. 9 and some of the other figures included herein.

Referring to FIG. 9 first, illustrated therein are a series of leads 26 which correspond to electrocardiograph leads I, II, $V_4$ and $V_6$. These leads are used to obtain electrocardiographic data from a test subject for whom it is desirous to predict the possibility of a future coronary episode.

The information obtained by probes 26 is fed into a macro-shock protection circuit 27, a safety feature incorporated to protect a test subject from the possibility of electrical shock. The output of this circuit is then suitably amplified and filtered by a preamplifier 28 and an amplifier 29, and a low pass filter 30, respectively. Because the raw electrocardiographic signal is in analog form, it is necessary that it first be converted to a suitable digital format prior to it being input into microcomputer 25. An A/D converter 31 performs this function.

As indicated by program step 32 of FIG. 10A, an electrocardiograph signal V(t) is measured for each of leads I, II, $V_4$ and $V_6$ over one complete cycle and stored by microcomputer 25 in a floppy disc storage 33, or alternatively, in an audio-cassette storage 34. For program execution purposes only, these electrocardiographic leads are then assigned lead numbers 1–4 as indicated at step 36.

Figure 3:
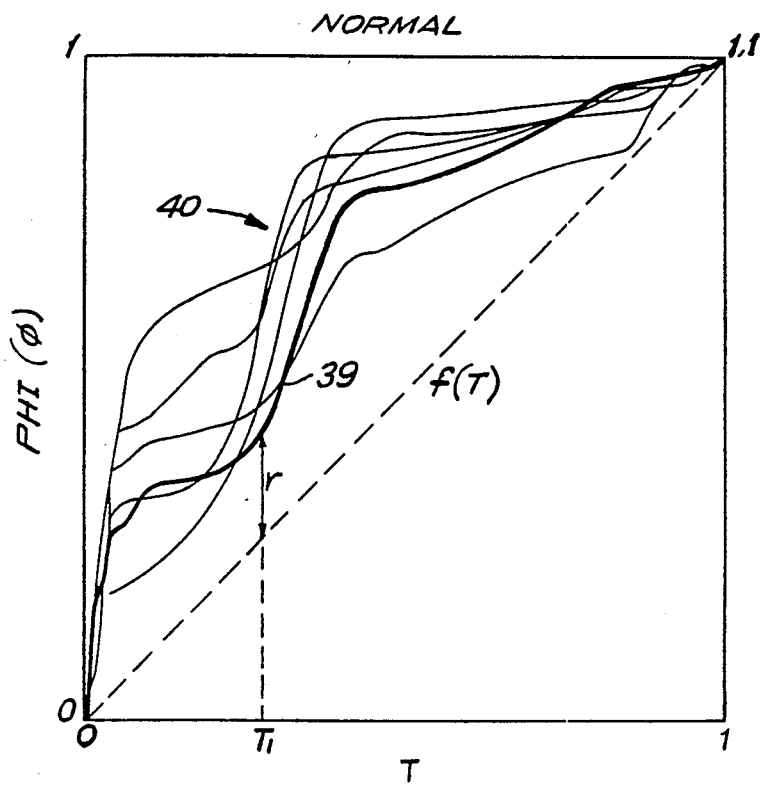
FIG. 3 illustrates the normalized integration of EKGs.

Taking the response signal for electrocardiographic lead I first, microcomputer 25 in accordance with the method of the invention integrates the absolute value of the electrocardiographic data over time (step 37). This integral is then normalized in step 38 by calculating $\phi$ in accordance with equation 1. An example of this calculation is illustrated in FIG. 3 by curve 39, depicted more heavily than similar curves 40 also illustrate therein. Using equation 2 and the pre-determined function f(T), microcomputer 25 then calculates the differences between f(T) and curve 39 for T=0−1 (step 41). The result, r, is the radius vector of the transformed electrocardiographic data obtained from the test subject.

Upon completing the calculations for the radius vector r, microcomputer 25 then computes the corresponding radius vector angle, $\theta$ using equation 3 for the values of T=0−1 (step 42). Once the polar coordinates r and $\theta$ have been calculated, they are plotted using a display unit 43, which may be an oscilloscope or an x-y plotter (step 44).

Operating in conjunction with a D/A converter 45, unit 43 traces a response signature 46 for curve 39 (shown in FIG. 4). Once this plot has been completed, point functions $P_1$, $P_2$ and $P_3$ are computed for signature 46 by microcomputer 25 as indicated by step 47. At step 48 signature 46 is then sumperimposed on the corresponding standard signature template for normal EKGs for lead I, which is similar to the template shown in FIG. 5.

The result as indicated by step 49, is then displayed via display unit 43. If the plot is within the corresponding template, a negative weight is assigned to lead I and stored by microcomputer 25 (step 50). Conversely, if the plot is outside the template a positive weight is assigned to lead I and stored for further use (step 51). Where neither condition is apparent, signature 46 is deemed inconclusive and assigned a weight of zero (step 52).

Thereafter, microcomputer 25 proceeds to superimpose the point functions calculated in step 47 on the point function plots for point functions $P_1$, $P_2$ and $P_3$ for lead I as generally indicated by routine 53. If a point function falls in pre-coronary region 22 it is assigned a positive weight and stored at step 54. In contrast, at 55 if a point function falls in the normal region 21, it is assigned a negative weight and stored. Where the point function falls in the no test region 23, microcomputer 25 assigns it a zero weight and stores the result (step 56).

As indicated previously, routine 53 is executed for point functions $P_1$, $P_2$ and $P_3$ for lead I. Thereafter, the above procedure is repeated in its entirely for leads II, $V_4$ and $V_6$. For each of these leads and their associated point functions weights are also calculated and stored. Once these calculations have been completed for all four electrocardiographic leads, microcomputer 25 adds the stored weights at step 57 and determines whether this sum (the Lundy index) is above, or below or equal to a particular cut off value (step 58). This value is selected according to the particular application in which the system is used. If the Lundy sum is less than or equal to the cut off value, the system indicates, as shown in step 59, that the test subject is a normal candidate. Conversely, if the sum is greater than the cut off value, the system indicates that the test subject is a coronary candidate (step 60).

Using a different embodiment, the present invention can also be used to characterize an individual as having either a normal or abnormal gait. An abnormal gait occurs where the individual has some form of joint dysfunction in one or both of his legs.

As in the previously described cardiographic embodiment of the present invention, a response signature of an unknown system state, i.e., the state of a test subject, is compared to a standard signature template representative of a known system state, i.e., a normal gait. This "normal" template is also developed for selected population samples in a manner similar to that used to develop template 14 shown in FIG. 5.

Figure 11:
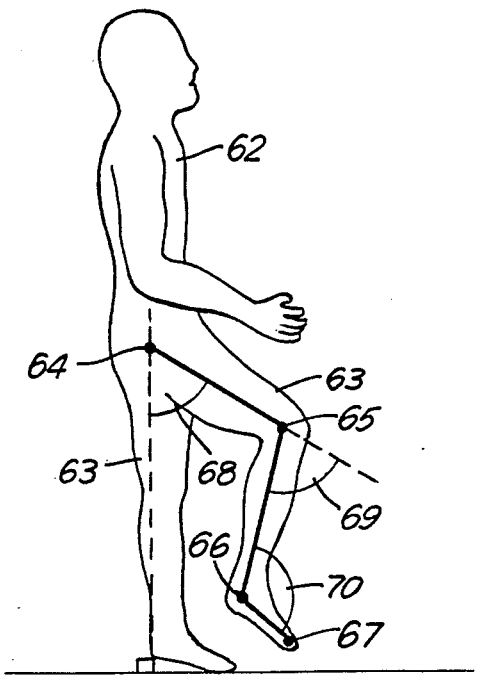
FIG. 11 illustrates the joint angles used to analyze the gait of a test subject.
Figure 12:
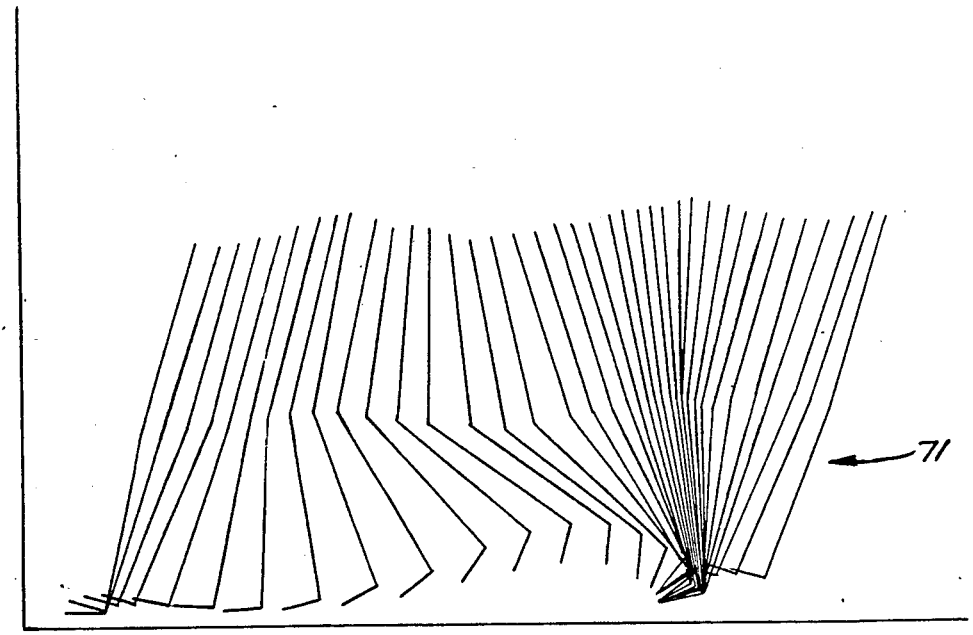
FIG. 12 illustrates a series of walk cycle steps comprising one complete walk cycle.
Figure 13:
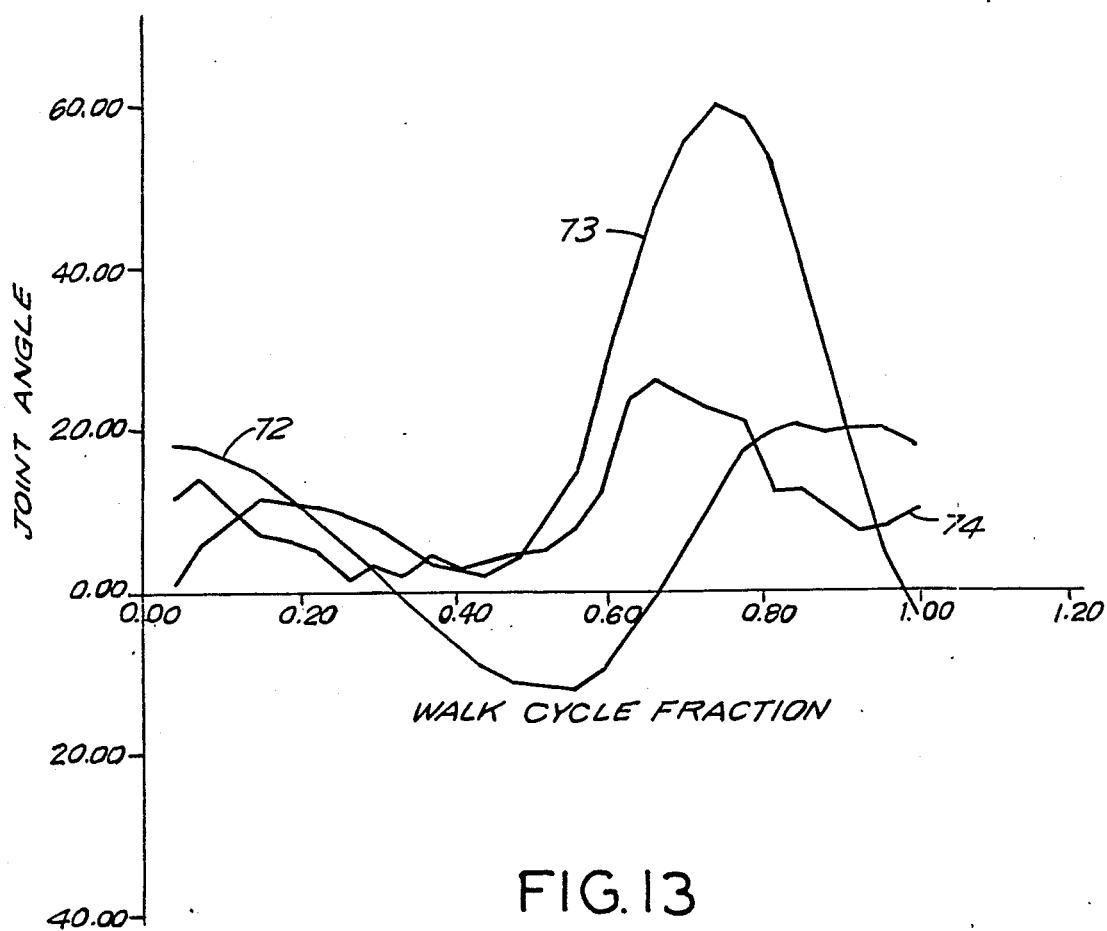
FIG. 13 illustrates a plot of the joint angles shown in FIG. 1 versus walk cycle fraction of a single walk cycle.

The data used to develop these signatures are obtained via photographic analysis. Referring to FIG. 11, the photographic analysis of a particular test subject 62 involves the taking of video recordings of the subject's gait pattern while the subject walks back and forth on a walkway at a comfortable pace. For this purpose reflective tags are placed at points of interest on each leg 63 of subject 62; specifically, the hip 64, knee 65, heel 66, and toe 67. From each picture frame taken, certain angles such as the hip joint angle 68, knee joint angle 69 and ankle joint angle 70 are calculated by a computer in the video system which is capable of detecting bright spots produced on the film by the reflective tags. This angle data is calculated over a single complete walk cycle 71, shown in FIG. 12. When plotted against fractions of a single walk cycle, this angle data produces a series of time varying curves, shown in FIG. 13, which can be analogized to the electrocardiogram signals V(t) shown in FIGS. 1 and 2. Curve 72 illustrates the changes that occur in hip joint angle 688 over a single walk cycle, while curves 73 and 74 illustrate the changes that occur in knee joint angle 72 and ankle joint angle 73, respectively, over the same single walk cycle.

Using the non-linear transformation defined in equations 1–3, a standard signature template representative of a normal gait may be developed for any population sample. A template of this type 75 shown in FIG. 14 was developed for analyzing normal left kness from a population sample consisting of 40 subjects ranging in age from 18 to 25 years. Like template 14 shown in FIG. 5, template 75 has an inner boundary 76 and an outer boundary 77, and includes one or more isoclines 78 similar to the isoclines 18 also shown in FIG. 5.

To analyze joint dysfunction in right knees, a similar template for normal right knees would be developed from the same population sample. Although the development of separate templates for left and right knees is preferred in practicing the invention, it has been found that because the normal templates for both knee joints are virtually identical, satisfactory results can be obtained when the same template is used to analyze joint dysfunction in both right and left knee joints. Thus, template 79 shown in FIG. 15 is identical to template 75 of FIG. 14, the inner boundary, outer boundary and isoclines thereof being designated with numerals 80, 81 and 82, respectively, in FIG. 15. It has been found that this similarity in shape can be used to detect early joint dysfunction in a test subject. If the response signature for each knee in a test subject fails to be identical to the other response signature, a degree of dysfunction is indicated.

Figure 14:
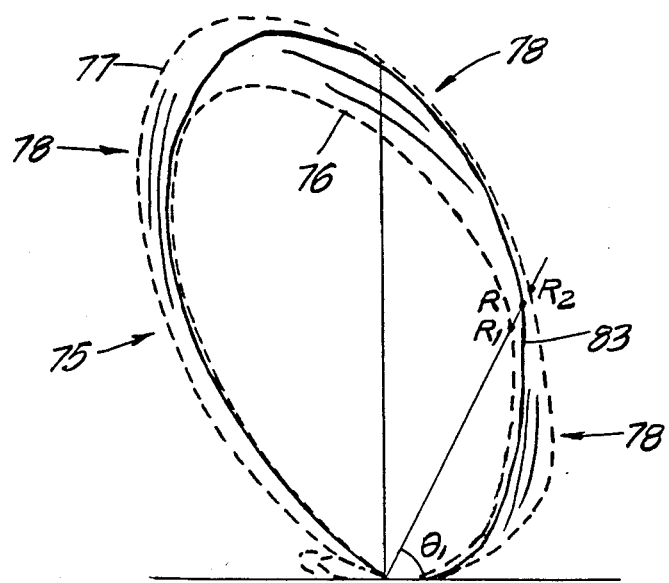
FIG. 14 illustrates a response signature representative of a normal gait for the left knee of a test subject, and the corresponding standard signature template therefor.
Figure 15:
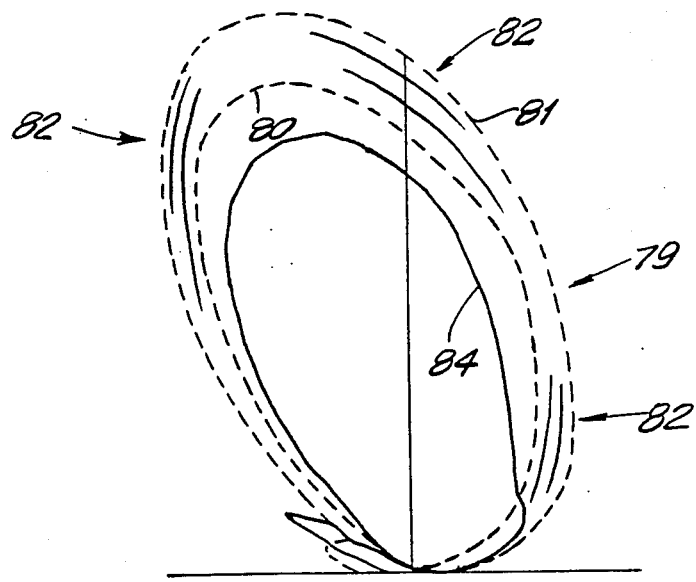
FIG. 15 illustrates a response signature representative of an abnormal gait for the right knee of a test subject, and the corresponding standard signature template therefor.

The response signatures for the two knee joints of a particular test subject are also shown in FIGS. 14 and 15. A response signature 83, obtained from the test subject's left knee, lies wholly within the bounded region of template 75 and does not cross any of the isoclines 78 therein. This indicates that the test subject's left knee is within a known state, i.e., no dysfunction is present.

Conversely, a response signature 84, obtained from the test subject's right knee, fails to lie wholly within the bounded region of template 79. This indicates that the test subject's right knee is in an unknown state, i.e., some degree of dysfunction is present. In this latter instance, the relative degree of departure of the unknown system state from the known system state may be evaluated using one or more point functions representative of the system being characterized. An illustrative example of such a point function by coordinates is the following:

P₄=(r, θ area), versus (r, θ perimeter)²

In this instance, a method virtually identical to the method described in the flow chart of FIGS. 10A and 10B, is used to calculate a Lundy index for the test subject's right knee to determine the extent of joint dysfunction therein. The system used to carry out this method would be similar to the system shown in FIG. 9, except that microcomputer 25 would receive joint angle data from a video recorder capable of sensing the bright spots produced on the film from the tags placed on the legs 66 of the test subject.

Figure 16:
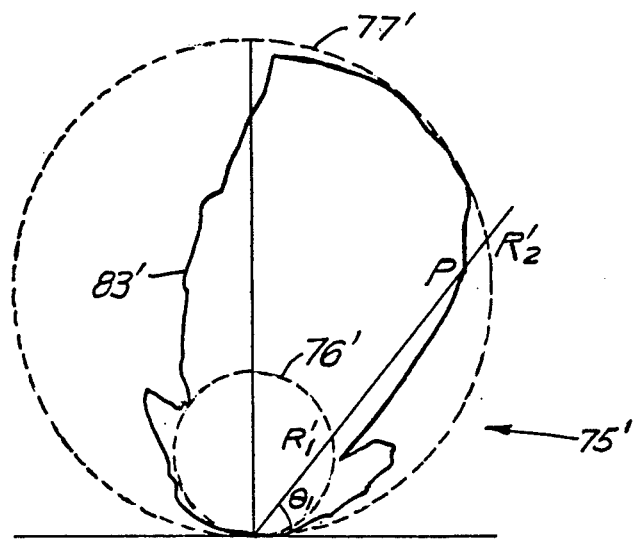
FIG. 16 illustrates a topological transformation of the data shown in FIG. 14.
Figure 17:
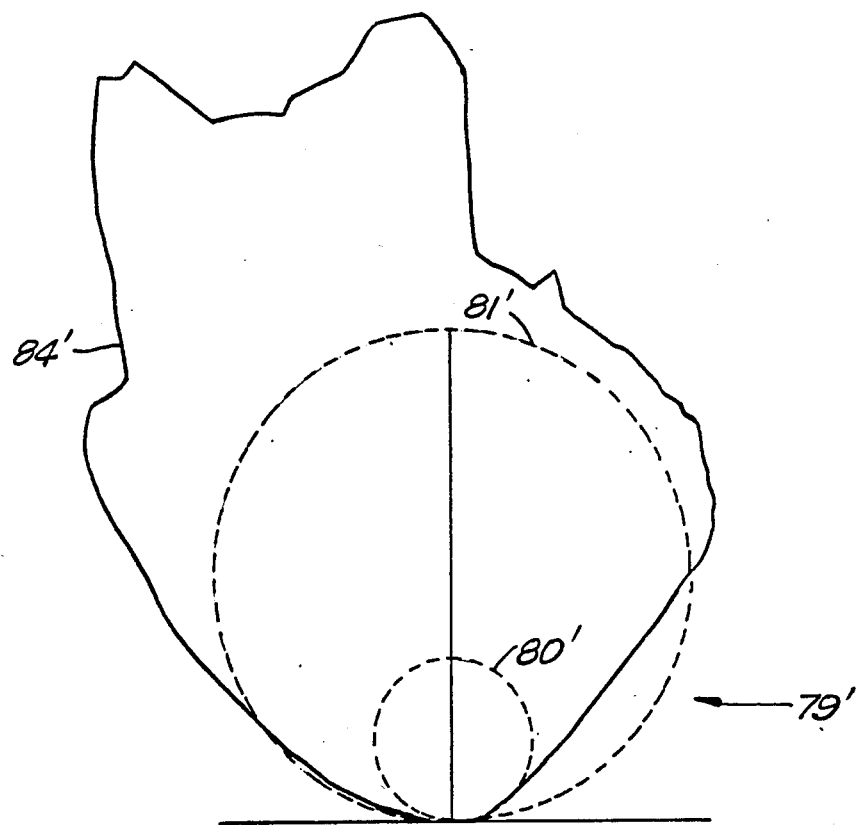
FIG. 17 illustrates a topological transformation of the data shown in FIG. 15.

It has also been found that the ability to detect slight joint dysfunctions, not readily perceivable, may be further enhanced by a topological transformation of a standard signature template, such as the templates 75 and 79 shown in FIGS. 14 and 15, respectively, into a normal template consisting of two internally tangent circles as shown in FIGS. 16 and 17. This transformation by necessity results in a similar transformation of any response signature ploted over the template.

The topological transformation of standard signature template 75 and response signature 83 of FIG. 14 is shown in FIG. 16 as template 75' consisting of tangent circles 76' and 77', and curve 83', respectively. Similarly, the topological transformation of template 79 and response signature 84 of FIG. 15 is shown in FIG. 17 as template 79' consisting of tangent circles 80' and 81', and curve 84'. The method used to produce this transformation can be illustrated by the following.

Referring to FIGS. 14 and 16, for any given angle $\theta_1$ a number of points can be identified on the polar plots shown in FIG. 14. A first point $R_1$ represents a radial coordinate corresponding to the inner boundary 76 of standard signature template 75. A second point $R_2$ also represents a radial coordinate of template 75, but one that corresponds to the outer boundary 77 thereof. A third point R is a generalized coordinate representative of response signature 83 lying somewhere between points $R_1$ and $R_2$.

Referring now to FIG. 16, as a result of a topological transformation of template 75, point $R_1$ moves to point $R_1'$, point $R_2$ moves to point $R_2'$ and point R moves to point $\rho$.

The location of $\rho$ can be defined by the following equation:

$$\rho_{\theta 1} = f_1(R_1) + (R - R_1)f_2(R) \quad (5)$$

Where $f_1$ and $f_2$ are appropriate weighting functions. It can readily be seen that $f_1(R_1) = R_1'$. Hence, $$\rho_{\theta 1} = R_1' + (R - R_1)f_2(R) \quad (6)$$

From this, it can be seen that $$f_2(R) = \frac{\rho_{\theta 1} - R_1'}{R - R_1} \quad (7)$$

but at $R = R_2$, $\rho_\theta = R_2'$, then $$f_2(R) = \frac{R_2' - R_1'}{R_2 - R_1} \quad (8)$$

then for any angle $$\rho_\theta = R_1' + (R - R_1)\frac{(R_2' - R_1')}{R_2 - R_1} \quad (9)$$

Equation (9) can be used to carry out the topological transformation of any response signature, such as response signature 83 shown in FIG. 14, in conjunction with the topological transformation of its corresponding template, such as the transformation of template 75 into template 75' shown in FIG. 16. This type of transformation enhances the visual perceptability, and thus the ability to characterize a physical system as being either in a known system state or an unknown system state.

It has also been found that it can sometimes be difficult to characterize the state of a physical system using the method of the present invention where a test subject's response signature is near the point of tangency between the two boundaries comprising the corresponding standard signature template. It has been found that for certain applications, this problem can be eliminated and the method of the present invention enhanced by offsetting from one another the inner and outer boundaries comprising a given standard signature template so as to eliminate the point of tangency between the two boundaries, and thereby, the ambiguity of whether a response signature plot near the region of tangency lies within or without the bounded region of the template. The boundary offset can be achieved by introducing one or more offset factors into the polar coordinates of the test data used to plot response signatures for test subjects and produce a corresponding standard signature template for such plot. Thus, polar coordinates r and θ are redefined as follows:

$$r = |\phi - f(T) + g_n| \quad (10)$$

$$\theta = 2\pi T \quad (11)$$

where $g_n$ may be any one of the following geometric measurements:

$$g_1 = \frac{\text{perimeter of } S_1}{\sqrt{\text{area of } S_1}}$$

$$g_2 = \frac{\text{arc length of } S_1}{\sqrt{\text{area of } S_1}}$$

where the arc length is a specified portion of the perimeter and where $S_1$ is the polar plot of any signal, such as plot 19 shown in FIG. 6;

$g_3 = r(T)$, at $T = \frac{1}{2}$, of $S_2$ $g_4 = $ perimeter of $S_2$ $g_5 = $ area under $S_2$ where $S_2$ is the plot of the non-linear transformation of any signal, such as plot 39 shown in FIG. 3;

$$g_6 = \frac{(\text{arc length of } S_3)^2}{\text{area of } S_3}$$

where $S_3$ is a time-varying test signal taken from a test subject, such as signals 11 and 12 shown in FIGS. 1 and 2, respectively;

$g_7$ = any combination of $g_1$ through $g_6$.

Figure 18:
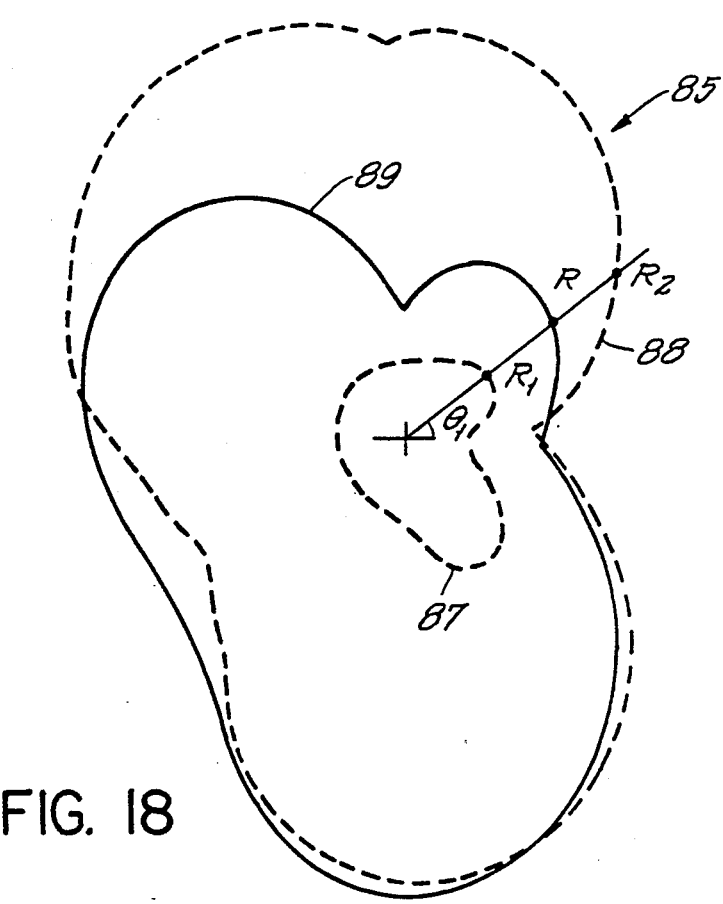
FIG. 18 illustrates a response signature representative of an abnormal gait for the left hip of a test subject, and a corresponding offset standard signature template therefor.
Figure 20:
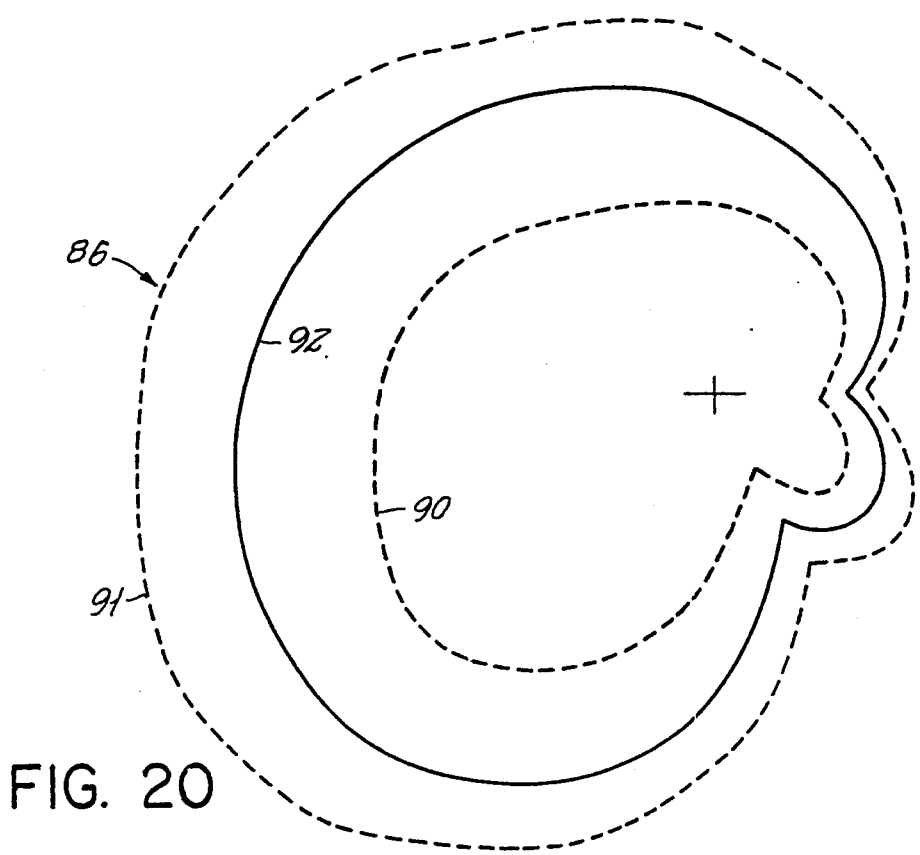
FIG. 20 illustrates a response signature representative of a normal gait for the left knee of a test subject, and a corresponding offset standard signature template therefor.

Although other offset factors different from those listed above could be used in carrying out the invention, it has been found that the values $g_1$-$g_7$ are generally preferred in practicing the invention. Two examples of offset standard signature templates, 85 and 86, which were generated using offset factor $g_1$, are shown in FIGS. 18 and 20, respectively. Template 85 of FIG. 18 if a left hip gait standard signature template which is comprised of an inner boundary 87 and an outer boundary 88 offset from one another so as to eliminate any point of tangency between them. Plotted over template 85 is a response signature 89 representative of the gait of the left hip of a test subject. Because boundaries 87 and 88 of template 85 have been offset from one another, a doctor reviewing plot 89 can readily ascertain that such plot fails to lie wholly within the bounded region of template 85, and therefore, that some joint dysfunction is present in the left hip of the test subject.

Template 86 of FIG. 20 is a left knee standard signature template which is also comprised of two boundaries, an inner boundary 90 and an outer boundary 91 offset from one another. Plotted within template 86 is a response signature 92 representative of the gait of the left knee of a test subject. Here again, because boundaries 90 and 91 have been offset with respect to one another, a doctor reviewing the plot can readily ascertain that response signature 92 lies wholly within the bounded region of template 86, and therefore, that the gait of the subject's left knee is normal.

Figure 19:
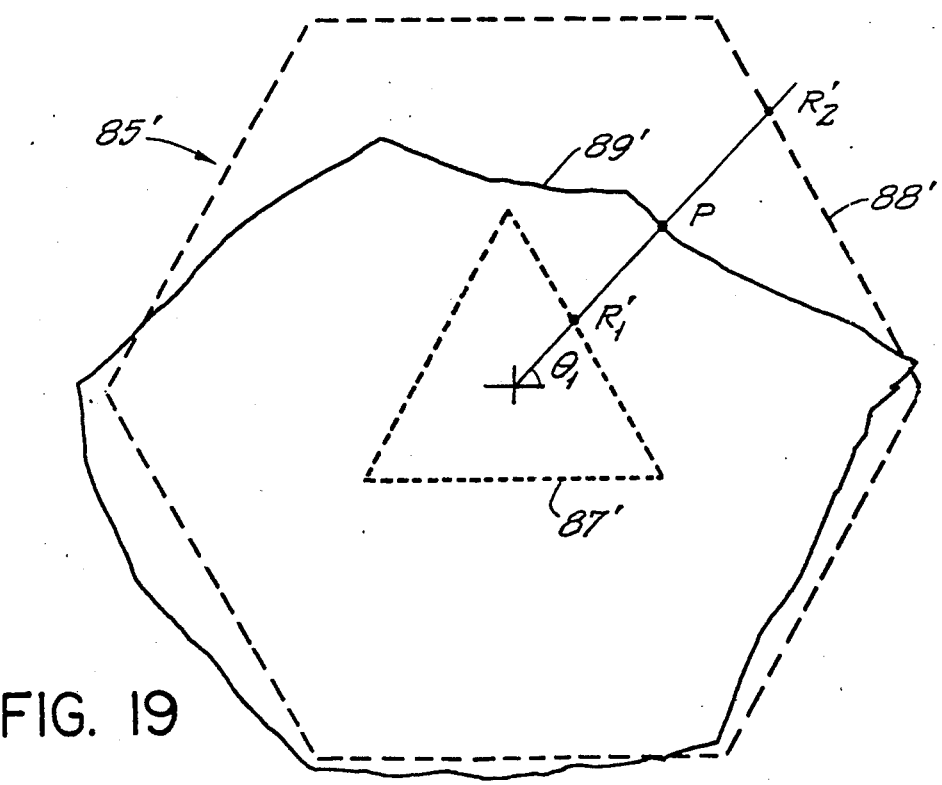
FIG. 19 illustrates an offset topological transformation of the data shown in FIG. 18.
Figure 21:
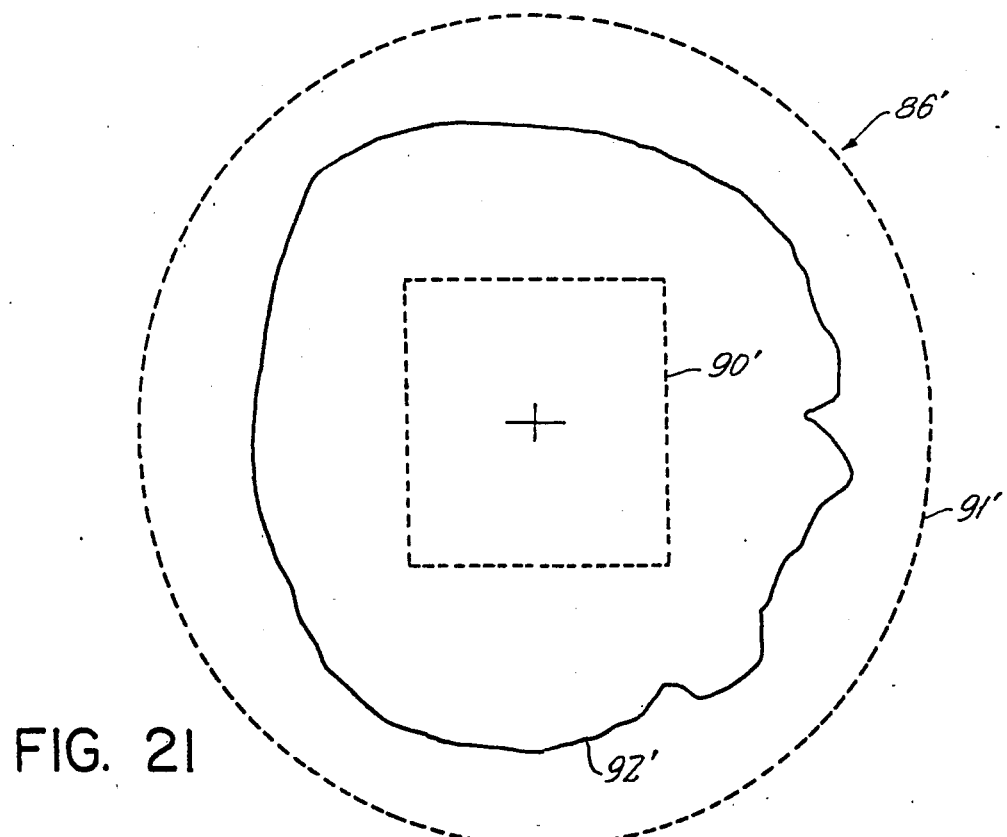
FIG. 21 illustrates an offset topological transformation of the data shown in FIG. 20.

It has also been found that the ability to characterize the state of a physical system may be further enhanced by a topological transformation of the offset standard signature template, such as templates 85 and 86 of FIGS. 18 and 20, into a normal offset template consisting of two concentric geometric patterns, as shown in FIGS. 19 and 21. It has been found that the preferred combinations consist of a triangle within a hexagon, or vice versa, and a square within a circle. Any such transformation by necessity results in a similar transformation of any response signature plotted over the template.

The topological transformations of offset signature template 85 and response signature 89 of FIG. 18 are shown in FIG. 19 as template 85', consisting of outer boundary hexagon 88' and inner boundary triangle 87' within and offset from hexagon 88', and response signature 89', respectively. Similarly, the topological transformations of template 86 and response signature 92 of FIG. 20 are shown in FIG. 21 as template 86', consisting of outer boundary circle 91' and inner boundary square 90' within and offset from circle 91', and response signature 92', respectively.

Previously disclosed equation (9) can be used to carry out any of the disclosed offset topological transformations for any response signature and its corresponding standard signature template. Thus, by way of example using equation (9) response signature 89 and template 85 of FIG. 18 are transformed into response signature 89' and template 85', respectively, of FIG. 19. This type of offset geometric transformation further enhances visual perceptability, and thus the ability to characterize a physical system as being either in a known system state or an unknown system state in accordance with the method of the present invention.

Other illustrative applications in which the present invention can be used to characterize the state of physical systems having a time varying history are radar and sonar systems, non-destructive testing and gas and oil exploration.

Non-destructive testing is different from destructive testing, which involves subjecting a product or structure to certain tests until it fails, e.g., where a metal member of a particular product becomes fatigued after the product performs a particular task repeatedly. The information obtained from such destructive testing can be used to develop a standard signature template, which can be used to monitor corresponding products or structures for the purpose of predicting their failure. When the response signature of a particular product or structure in actual service fails to fall within the standard signature template representative of similar products or structures in good operating condition, the unit under test can be flagged as being likely to fail within a certain period of time.

Where the present invention is used in the exploration for gas and oil reserves, a standard signature template corresponding to exploration sites having sufficient oil or gas reserves large enough for commercial exploitation can be developed from data obtained from previous satisfactory sites. A response signature for a particular exploration site is obtained from the seismographic traces generated by exploration blasts. Such seismographs are currently used to identify "desirable" drilling sites; however, since the success rate of this method is limited, the present invention can be used to locate desirable sites more successfully.

The above-described embodiments of the invention are illustrative and modifications thereof may occur to those skilled in the art. The invention is not limited to the embodiments disclosed herein, but is to be limited only as defined by the appended claims.

TABLE 1

| CASE NO. | TEMPLATE LEAD | | | | POINT FUNCTION | | | SUM OR LUNDY INDEX | DIAGNOSIS |
|---|---|---|---|---|---|---|---|---|---|
| | I | II | $V_4$ | $V_6$ | $P_1$ | $P_2$ | $P_3$ | | |
| 1 | +1 | +1 | −1 | +1 | +1 | 0 | +1 | +10 | C* |
| 2 | −1 | +1 | +1 | 0 | +1 | +1 | +1 | +12 | C |
| 3 | 0 | +1 | +1 | −1 | +1 | −1 | 0 | +8 | C |
| 4 | +1 | −1 | −1 | −1 | −1 | −1 | +1 | −7 | N** |
| 5 | −1 | −1 | −1 | +1 | 0 | +1 | −1 | −11 | N |
| 6 | −1 | 0 | −1 | +1 | −1 | +1 | 0 | −5 | N |
| Weight | 2 | 5 | 3 | 1 | 2 | 1 | 3 | | |

*Coronary candidate
**Normal subject

What is claimed is:

1. A method for characterizing the unknown state of a physical system with reference to like physical systems in a known state comprising the steps of:
   obtaining an offset standard signature representative of the known system state including subjecting a plurality of data signals representative of a pre-determined characteristic of the known system state which are obtained from said like physical systems to a pre-defined non-linear coordinate transformation, adjusting said transformation of said plurality of data signals by an offset factor and constructing an offset standard signature template from a composite of said plurality of transformed and offset data signals, said offset standard signature including a primary signature comprising a closed multi-dimensional region within a pre-defined coordinate system having an inner boundary and an outer boundary offset from said inner boundary, and a second signature comprising at least one isocline situated within said region;

obtaining an offset response signature representative of the unknown system state including subjecting a data signal representative of said pre-determined characteristic of the unknown system state to said pre-defined non-linear coordinate transformation, adjusting said transformation of said data signal by said offset factor and constructing an offset response signature plot from said transformed and offset data signal;

determining whether the system being characterized is in the known state by comparing said offset response signature to said offset standard signature including effecting an overlay of said offset plot over said offset template; and if the system being characterized is not in the known state, evaluating the relative degree of departure of the system being characterized therefrom.

2. A method as recited in claim 1 wherein said steps of obtaining said offset standard signature and said offset response signature are further comprised of subjecting said offset standard signature template and said offset response signature plot to a pre-defined topological transformation so that said offset standard signature template is in the form of two concentric geometric figures offset from one another.

3. A method for characterizing an unknown state of a physical system with reference to like physical systems in a known state comprising the steps of:

obtaining an offset standard signature representative of the known system state including subjecting a plurality of data signals representative of a pre-determined characteristic of the known system state to a pre-defined non-linear coordinate transformation, adjusting said transformation of said plurality of data signals by an offset factor, and constructing an offset standard signature template including a primary signature comprising a closed two-dimensional region within a pre-defined coordinate system having an inner boundary and an outer boundary offset from one another and a secondary signature comprising a plurality of isoclines situated within said region from a composite of said plurality of transformed and offset data signals;

obtaining an offset response signature representative of the unknown system state including subjecting a data signal representative of said pre-determined characteristic of the unknown system state to said pre-defined non-linear coordinate transformation, adjusting said transformation of said data signal by said offset factor, and constructing an offset response signature plot from said transformed and offset data signal;

comparing said offset response signature to said offset standard signature to determine whether said offset response signature lies wholly within said closed region or crosses any of said isoclines situated within said region including effecting an overlay of said offset plot over said offset template;

assigning said offset response signature a pre-determined negative weight if said offset response signature is wholly within said closed region and does not cross any of said isoclines, or a pre-determined positive weight if said offset response signature lies wholly or partially outside said closed region or crosses any of said isoclines;

calculating and plotting a plurality of pre-defined point functions representative of systems in the known system state;

calculating and plotting a plurality of pre-defined point functions representative of systems not in the known system state;

calculating a plurality of pre-defined point functions representative of the system being characterized;

comparing said point functions for said system being characterized with said point functions for said systems in the known system state, and for systems not in the known system state;

multiplying said point functions for said system being characterized by a negative pre-defined weighting factor if it falls within said plot of said point functions for systems in the known state, or by a positive pre-defined weighting factor if it falls within the plot of said point functions for systems not in the known state, or by a weighting factor of zero if it falls in neither plot;

summing said weighted response signature and said weighted point functions to obtain a number; and comparing said number to a pre-determined cut-off value to determine if the system being characterized is in the known state.

4. A method as recited in claim 3 wherein said steps of obtaining said offset standard signature and said offset response signature are further comprised of subjecting said offset standard signature template and said offset response signature plot to a pre-determined topological transformation so that said offset standard signature template is in the form of two concentric geometric figures offset from one another.

5. A method as recited in claims 2 or 4 wherein one of said geometric figures is a triangle and the other of said geometric figures is a hexagon.

6. A method as recited in claims 2 or 4 wherein one of said geometric figures is a square and the other of said geometric figures is a circle.

7. A method as recited in claims 1, 2, 3 or 4 wherein said transformations of said plurality of data signals and said data signal are each comprised of a plurality of coordinate pairs;

wherein said step of adjusting said transformation of said plurality of data signals by said offset factor is comprised of doubling a first coordinate of each of said coordinate pairs, and adding at least one geometric measurement of each of said data signals to a second coordinate of each of said coordinate pairs; and wherein said step of adjusting said transformation of said data signal by said offset factor is comprised of doubling a first coordinate of each of said coordinate pairs, and adding at least one geometric measurement of said data signal to a second coordinate of each of said coordinate pairs.

8. An apparatus as recited in claim 7 further comprising means for subjecting said offset standard signature template and said offset response signature plot to a pre-defined topological transformation so that said offset standard signature template is in the form of two concentric geometric figures.

9. An apparatus as recited in claim 8 wherein said transformations of said plurality of data signals and said data signal are each comprised of a plurality of coordinate pairs;
wherein said means for adjusting said transformation of said plurality of data signals by said offset factor is comprised of means for doubling a first coordinate of each of said coordinate pairs, and means for adding at least one geometric measurement of each of said data signals to a second coordinate of each of said coordinate pairs; and
wherein said means for adjusting said transformation of said data signal by said offset factor is comprised of means for doubling a first coordinate of each of said coordinate pairs, and means for adding at least one geometric measurement of said data signal to a second coordinate of each of said coordinate pairs.

10. An apparatus as recited in claim 8 wherein said transformations of said plurality of data signals and said data signal are each comprised of a plurality of coordinate pairs;
wherein said means for adjusting said transformation of said plurality of data signals by said offset factor is comprised of means for doubling a first coordinate of each of said coordinate pairs, and means for adding at least one geometric measurement of said transformation of said plurality of data signals to a second coordinate of each of said coordinate pairs; and
wherein said means for adjusting said transformation of said data signal by said offset factor is comprised of means for doubling a first coordinate of each of said coordinate pairs, and means for adding at least one geometric measurement of said transformation of said data signal to a second coordinate of each of said coordinate pairs.

11. A method as recited in claim 8 wherein said transformations of said plurality of data signals and said data signal are each comprised of a plurality of coordinate pairs;
wherein said means for adjusting said transformation of said plurality of data signals by said offset factor is comprised of means for doubling a first coordinate of each of said coordinate pairs, and means for adding at least one geometric measurement of each of said plurality of data signals and at least one geometric measurement of said transformation of said plurality of data signals to a second coordinate of each of said coordinate pairs; and
wherein said means for adjusting said transformation of said data signal by said offset factor is comprised of means for doubling a first coordinate of each of said coordinate pairs, and means for adding at least one geometric measurement of said data signal and at least one geometric measurement of said transformation of said plurality of data signals to a second coordinate of each of said coordinate pairs.

12. A method as recited in claims 1, 2, 3 or 4 wherein said transformations of said plurality of data signals and said data signal are each comprised of a plurality of coordinate pairs;
wherein said step of adjusting said transformation of said plurality of data signals by said offset factor is comprised of doubling a first coordinate of each of said coordinate pairs, and adding at least one geometric measurement of said transformation of said plurality of data signals to a second coordinate of each of said coordinate pairs; and
wherein said step of adjusting said transformation of said data signal by said offset factor is comprised of doubling a first coordinate of each of said coordinate pairs, and adding at least one geometric measurement of said transformation of said data signal to a second coordinate of each of said coordinate pairs.

13. An apparatus as recited in claim 12 wherein one of said geometric figures is a triangle and the other of said geometric figures is a hexagon.

14. An apparatus as recited in claim 12 wherein one of said geometric figures is a square and the other of said geometric figures is a circle.

15. A method as recited in claims 1, 2, 3 or 4 wherein said transformations of said plurality of data signals and said data signal are each comprised of a plurality of coordinate pairs;
wherein said step of adjusting said transformation of said plurality of data signals by said offset factor is comprised of doubling a first coordinate of each of said coordinate pairs and adding at least one geometric measurement of each of said plurality of data signals and at least one geometric measurement of said transformation of said plurality of data signals to a second coordinate of each of said coordinate pairs; and
wherein said step of adjusting said transformation of said data signal by said offset factor is comprised of doubling a first coordinate of each of said coordinate pairs, and adding at least one geometric measurement of said data signal and at least one geometric measurement of said transformation of said plurality of data signals to a second coordinate of each of said coordinate pairs.

16. An apparatus for characterizing the unknown state of a physical system with reference to like physical systems in a known state comprising:
means for measuring a plurality of data signals representative of a pre-determined characteristic of the known system state, and a data signal representative of said pre-determined characteristic of the unknown system state;
means for calculating pre-determined non-linear coordinate transformations of said plurality of data signals and said data signal, each of said transformations comprising a plurality of coordinate pairs;
means for adjusting said transformation of said plurality of data signals by said offset factor comprising means for doubling a first coordinate of each of said coordinate pairs, and means for adding at least one geometric measurement of each of said data signals to a second coordinate of each of said coordinate pairs to form an offset standard signature template representative of the known system state;
means for adjusting said transformation of said data signal by said offset factor comprising means for doubling a first coordinate of each of said coordinate pairs, and means for adding at least one geometric measurement of said data signal to a second coordinate of each of said coordinate pairs to form an offset response signature plot representative of the unknown system state;

means for comparing said offset response signature plot to said offset standard signature template to determine whether the system being characterized is in the known state; and means for evaluating the relative degree of departure from the known state if the system being characterized is not in the known state.

17. An apparatus for characterizing the unknown state of a physical system with reference to like physical systems in a known state comprising:

means for measuring a plurality of data signals representative of a pre-determined characteristic of the known system state, and a data signal representative of said pre-determined characteristic of the unknown system state;

means for calculating pre-determined non-linear coordinate transformations of said plurality of data signals and said data signal, each of said transformations comprising a plurality of coordinate pairs;

means for adjusting said transformation of said plurality of data signals by said offset factor comprising means for doubling a first coordinate of each of said coordinate pairs, and means for adding at least one geometric measurement of said transformation of said plurality of data signals to a second coordinate of each of said coordinate pairs to form an offset standard signature template representative of the known system state;

means for adjusting said transformation of said data signal by said offset factor comprising means for doubling a first coordinate of each of said coordinate pairs, and means for adding at least one geometric measurement of said transformation of said data signal to a second coordinate of each of said coordinate pairs to form an offset response signature plot representative of the unknown system state;

means for comparing said offset response signature plot to said offset standard signature template to determine whether the system being characterized is in the known state; and means for evaluating the relative degree of departure from the known state if the system being characterized is not in the known state.

18. An apparatus for characterizing the unknown state of a physical system with reference to like physical systems in a known state comprising:

means for measuring a plurality of data signals representative of a pre-determined characteristic of the known system state, and a data signal representative of said pre-determined characteristic of the unknown system state;

means for calculating pre-determined non-linear coordinate transformations of said plurality of data signals and said data signal, each of said transformations comprising a plurality of coordinate pairs;

means for adjusting said transformation of said plurality of data signals by said offset factor comprising means for doubling a first coordinate of each of said coordinate pairs, and means for adding at least one geometric measurement of each of said plurality of data signals and at least one geometric measurement of said transformation of said plurality of data signals to a second coordinate of each of said coordinate pairs to form an offset standard signature template representative of the known system state;

means for adjusting said transformation of said data signal by said offset factor comprising means for doubling a first coordinate of each of said coordinate pairs, and means for adding at least one geometric measurement of said data signal and at least one geometric measurement of said transformation of said plurality of data signals to a second coordinate of each of said coordinate pairs to form an offset response signature plot representative of the unknown system state;

means for comparing said offset response signature plot to said offset standard signature template to determine whether the system being characterized is in the known state; and means for evaluating the relative degree of departure from the known state if the system being characterized is not in the known state.

* * * * *

UNITED STATES PATENT AND TRADEMARK OFFICE
CERTIFICATE OF CORRECTION

PATENT NO. : 4,665,485
DATED : May 12, 1987
INVENTOR(S) : Joseph R. Lundy, et al.

It is certified that error appears in the above-identified patent and that said Letters Patent is hereby corrected as shown below:

Column 1, line 30, "as" should be --has--.

Column 2, line 63, "Fig. 1" should be --Fig. 11--.

Column 4, equation 1, "$t_0{}^t$" should be --$\int_{t_0}^{t}$--.

Column 4, equation 1, "$t_0{}^{t_1}$" should be --$\int_{t_0}^{t_1}$--.

Column 7, line 64, "(2)(-1)+5(+1)+(3)" should be --(2)(-1)+(5)(+1)+(3)--.

Column 7, line 65, "(+1)+(1)(0)+2(+1)(3)(1)" should be --(+1)+(1)(0)+(2)(+1)+(1)(+1)+(3)(+1)--.

Column 8, line 26, "intergration" should be --integration--.

Column 8, line 65, "illustrate" should be --illustrated--.

Column 10, line 20, "688" should be --68--.

Column 10, line 22, "72" should be --69-- and "73" should be --70--.

Column 11, equation 8, "$R_2^1 = R_1^1$" should be --$R_2^1 - R_1^1$--.

Column 13, line 11, "if" should be --is--.

Signed and Sealed this

First Day of March, 1988

*Attest:*

DONALD J. QUIGG

*Attesting Officer*   *Commissioner of Patents and Trademarks*

UNITED STATES PATENT AND TRADEMARK OFFICE
CERTIFICATE OF CORRECTION

PATENT NO. : 4,665,485
DATED : May 12, 1987
INVENTOR(S) : Joseph R. Lundy et al.

It is certified that error appears in the above-identified patent and that said Letters Patent is hereby corrected as shown below:

Claim 8, line 1, "claim 7" should be --claims 16, 17 or 18--.

Claim 13, line 1, "claim 12" should be --claim 8--.

Claim 14, line 1, "claim 12" should be --claim 8--.

Signed and Sealed this

Fourteenth Day of June, 1988

Attest:

DONALD J. QUIGG

*Attesting Officer*     *Commissioner of Patents and Trademarks*